(12) United States Patent
Horii et al.

(10) Patent No.: US 11,786,208 B2
(45) Date of Patent: *Oct. 17, 2023

(54) BIOLOGICAL SOUND SENSOR AND BIOLOGICAL SOUND DIAGNOSTIC DEVICE

(71) Applicant: PANASONIC INTELLECTUAL PROPERTY MANAGEMENT CO., LTD., Osaka (JP)

(72) Inventors: Noriaki Horii, Kyoto (JP); Keisuke Taira, Ehime (JP); Kazuhiko Inokuchi, Ehime (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 750 days.

This patent is subject to a terminal disclaimer.

(21) Appl. No.: 16/828,459

(22) Filed: Mar. 24, 2020

(65) Prior Publication Data

US 2020/0222004 A1 Jul. 16, 2020

Related U.S. Application Data

(63) Continuation of application No. 14/702,587, filed on May 1, 2015, now Pat. No. 10,631,786.

(30) Foreign Application Priority Data

May 15, 2014 (JP) .................................. 2014-101766

(51) Int. Cl.
*A61B 7/04* (2006.01)
*A61B 5/00* (2006.01)
(Continued)

(52) U.S. Cl.
CPC .............. *A61B 7/04* (2013.01); *A61B 5/6833* (2013.01); *A61B 5/72* (2013.01); *A61B 5/742* (2013.01);
(Continued)

(58) Field of Classification Search
CPC ........... A61B 7/04; A61B 5/6833; A61B 5/72; A61B 5/742; A61B 7/02;
(Continued)

(56) References Cited

U.S. PATENT DOCUMENTS 4,239,046 A 12/1980 Ong
6,280,814 B1 8/2001 Offermann et al.
(Continued)

FOREIGN PATENT DOCUMENTS

GB 2507113 4/2014
JP 52-038492 3/1977
(Continued)

OTHER PUBLICATIONS

The Extended European Search Report dated Oct. 12, 2015 for the related European Patent Application No. 15166939.7.

*Primary Examiner* — Patrick Fernandes
(74) *Attorney, Agent, or Firm* — GREENBLUM & BERNSTEIN, P.L.C.

(57) ABSTRACT

A biological sound sensor to be used in contact with a skin of a living body, and includes a casing that has an opening in a face on the side facing the skin of the living body, a double-sided adhesive membrane having a first surface and a second surface, the second surface closes the opening by adhering to the face of the casing and the first surface adheres to the skin when collecting a biological sound produced in the living body. A microphone is arranged in the casing and picks up the biological sound. The double-sided adhesive membrane has a one-material portion, made of the first adhesive material, through the double-sided adhesive membrane from the first surface to the second surface.

19 Claims, 12 Drawing Sheets

(51) Int. Cl.
*A61B 7/02* (2006.01)
*H04R 1/14* (2006.01)
*G01H 1/00* (2006.01)

(52) U.S. Cl.
CPC ........ *A61B 7/02* (2013.01); *A61B 2560/0475* (2013.01); *A61B 2562/0204* (2013.01); *A61B 2562/06* (2013.01); *G01H 1/00* (2013.01); *H04R 1/14* (2013.01)

(58) Field of Classification Search
CPC .... A61B 2560/0475; A61B 2562/0204; A61B 2562/16; G01H 1/00; H04R 1/14
See application file for complete search history.

(56) References Cited

U.S. PATENT DOCUMENTS

| | | |
|---|---|---|
| 2002/0055684 A1 | 5/2002 | Patterson |
| 2004/0032957 A1 | 2/2004 | Mansy et al. |
| 2007/0113649 A1 | 5/2007 | Bharti et al. |
| 2013/0028462 A1 | 1/2013 | Chen |
| 2013/0158435 A1 | 6/2013 | Endo et al. |
| 2014/0303521 A1 | 10/2014 | Nakamura et al. |

FOREIGN PATENT DOCUMENTS

| | | |
|---|---|---|
| JP | 2007-209610 | 8/2007 |
| JP | 2008-042741 | 2/2008 |
| JP | 2008-302052 | 12/2008 |
| JP | 2009-517127 | 4/2009 |
| JP | 4671290 | 4/2011 |
| JP | 2013-103040 | 5/2013 |
| WO | 9118738 | 12/1991 |
| WO | 2013/073311 | 5/2013 |

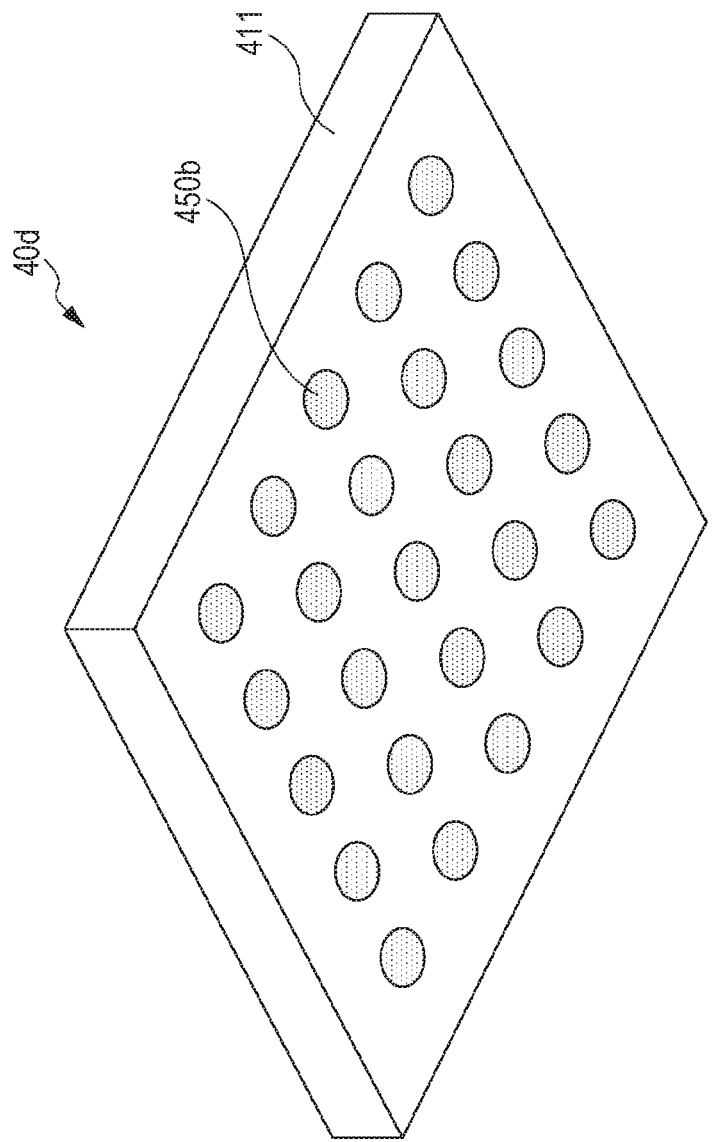

BIOLOGICAL SOUND SENSOR AND BIOLOGICAL SOUND DIAGNOSTIC DEVICE

CROSS REFERENCE TO RELATED APPLICATIONS

This is a Continuation Application of U.S. patent application Ser. No. 14/702,587, filed May 1, 2015, which claims priority to Japanese Patent Application No. 2014-101766 filed on May 15, 2014. The disclosures of the above-mentioned documents are incorporated by reference herein in their entireties.

BACKGROUND

1. Technical Field

The present disclosure relates to a biological sound sensor to measure a biological sound by being fixed to a skin surface of a living body and a biological sound diagnostic device that uses the biological sound sensor.

2. Description of the Related Art

Development of biological sound sensors to measure a biological sound for a diagnosis of a disease in a circulatory system and a respiratory system has been advanced. Although such biological sound sensors include a type of sensor that collects a biological sound by using a microphone, there has been a problem that such a sensor is likely to collect an ambient noise, which results in a reduction in a signal-to-noise ratio (SN ratio) with respect to a biological sound in a noise environment. Thus, efforts to cut the ambient noise by improving a casing which holds a microphone have been made (for example, see Japanese Patent No. 4671290).

SUMMARY

However, there is a desire to further improve a biological sound sensor described in the above-described Japanese Patent No. 4671290.

In one general aspect, the techniques disclosed here feature a biological sound sensor to be used in contact with a skin of a living body and includes a casing that has an opening in a face on the side facing the skin of the living body, a double-sided adhesive membrane both surfaces of which have adhesion, one surface of which closes the opening by adhering to the face of the casing, and the other surface of which adheres to the skin when collecting a biological sound produced in the living body, and a microphone that is arranged in the casing and picks up the biological sound. The double-sided adhesive membrane includes a one-material portion that is made from a single type of material across the entire width in the thickness direction and is made from an adhesive material having adhesion.

By the present disclosure, a further improvement has been achieved.

These general and specific aspects may be implemented using a system, a method, and a computer program, and any combination of systems, methods, and computer programs.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 12 is an enlarged partly cutaway perspective view illustrating a portion of another double-sided adhesive membrane according to the other embodiment 3.

DETAILED DESCRIPTION (Underlying Knowledge Forming Basis of the Present Disclosure)

The inventor found that the following problems might occur concerning the biological sound sensor described in "Description of the Related Art" section.

The biological sound sensor (transmitted sound pickup microphone) described in Japanese Patent No. 4671290 includes an inner cover and an outer cover, as a casing, that are container-shaped members and have open faces on the side contacting a skin surface, has a microphone contained in the casing, and has the inside of the covers filled with a flexible member (adhesive member) without space. The inner cover and the outer cover have portions that contact the skin.

As described above, in the biological sound sensor described in Japanese Patent No. 4671290, because the inner cover and the outer cover have portions contacting the skin and the portions are made of resin, plastic, metal, or the like, there is such a problem that the portions do not follow deformation of a skin surface, and the biological sound sensor is likely to separate from the skin surface of a living body from the portions as a starting point.

Because multiple uses of the biological sound sensor described in Japanese Patent No. 4671290 cause such problems that adhesion weakens, multiple uses are not desirable from the viewpoint of sanitation, and so on, the inside of the covers may be newly refilled with the flexible member. However, because a microphone is embedded in the flexible material, it is difficult to replace the flexible member without removing the microphone. In other words, the biological sound sensor has a structure that makes it difficult to replace a flexible member therein without influencing the performance of a microphone.

For the biological sound sensor (transmitted sound pickup microphone) described in Japanese Patent No. 4671290, a study to increase sound insulation performance by filling the interspace between the microphone and the casing with a flexible member has been conducted. However, even if the casing is filled with a flexible member, it is supposed that an improvement in the sound insulation performance against an ambient noise is limited. That is because the intensity of an ambient noise propagated to the microphone through the casing is intrinsically limited due to a large difference in an acoustic impedance at the boundary surface between the air layer, through which the ambient noise is propagated, and the casing. Therefore, it is necessary to cut an ambient noise by a method other than an improvement in the casing.

An object of the present disclosure is to provide a double-sided adhesive membrane that makes it possible to cut an ambient noise specifically while measuring the signal intensity of a biological sound, which is used in a diagnosis, with a high sensitivity.

Figure 1:
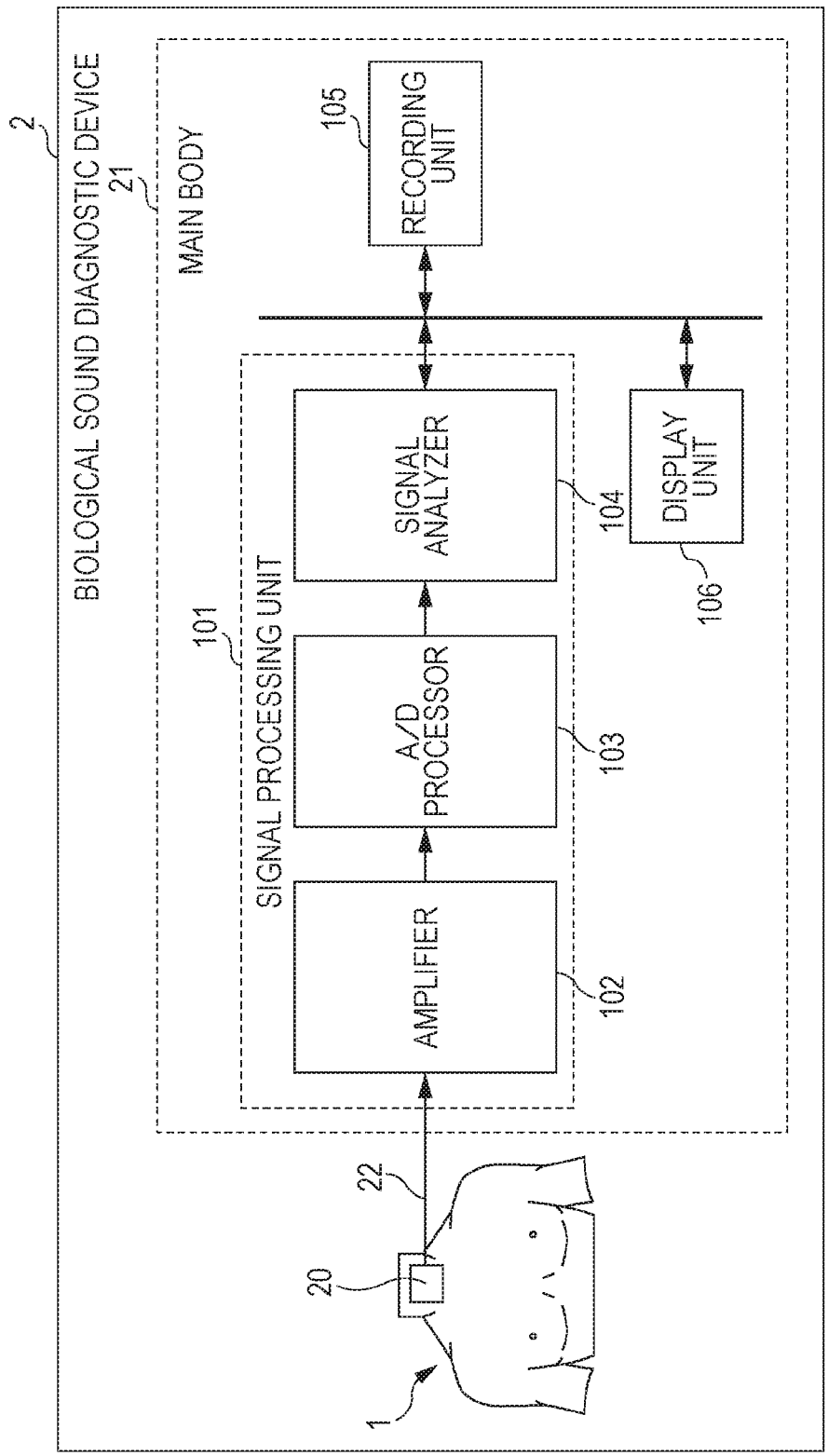
FIG. 1 is a diagram illustrating a configuration of a biological sound diagnostic device.

FIG. 1 is a diagram illustrating a configuration of a biological sound diagnostic device 2. Although a living body 1, which is a subject, is illustrated in FIG. 1, the living body 1 is not included in the configuration of the biological sound diagnostic device 2. The biological sound diagnostic device 2 includes a biological sound sensor 20, a main body 21, and a signal cable 22, through which a biological sound is transmitted from the biological sound sensor 20 to the main body 21. The biological sound sensor 20 collects biological sounds produced in the living body 1 while being attached to the living body 1 (for example, cervical region) and in contact with a skin of the living body 1. The biological sound collected by the biological sound sensor 20 is converted into an analog signal, transmitted to the main body 21 via the signal cable 22, and then conducted A/D conversion and analyzed in the main body 21. That is, the main body 21 analyzes the biological sound collected by the biological sound sensor 20 and outputs an analyzed result. Although a signal measured by the biological sound sensor 20 is transmitted to the main body 21 via the signal cable 22 through a wire connection between the biological sound sensor 20 and the main body 21, the signal may be transmitted by wireless communication.

Specifically, the main body 21 includes a signal processing unit 101, a recording unit 105 that records information to be used by the signal processing unit 101 and an analysis result of a biological sound signal, and a display unit 106 that displays the analysis result of the biological sound signal for a measurer. The signal processing unit 101 includes an amplifier 102 that amplifies the biological sound signal measured by the biological sound sensor 20, an ND processor 103 that performs A/D conversion to digitalize (convert into a digital signal) the biological sound signal amplified by the amplifier 102, and a signal analyzer 104 that analyzes the biological sound signal converted into a digital signal by the ND processor 103. The recording unit 105 and the display unit 106 may be arranged in an outside device, which is connected by a communication line.

Figure 2:
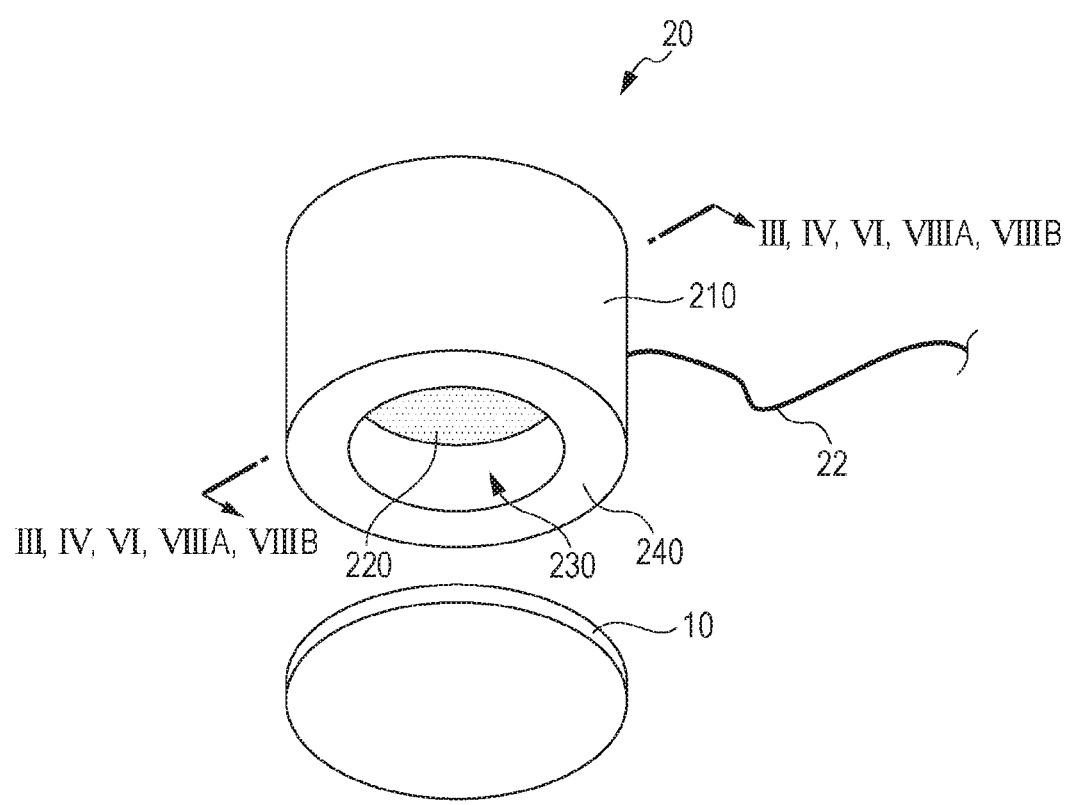
FIG. 2 is a perspective view illustrating a biological sound sensor when viewed obliquely from the lower side thereof (from a face on the skin side)

FIG. 2 is a perspective view illustrating a biological sound sensor when viewed obliquely from the lower side (from a face on the skin side).

As illustrated in FIG. 2, the biological sound sensor 20 includes a casing 210 that has a cylindrical external shape, a microphone 220, and a double-sided adhesive membrane 10. The casing 210 has an opening 230 in a face 240, which is located on the side contacting a skin of a living body. The microphone 220 is arranged in the casing 210 and picks up a sound. The double-sided adhesive membrane 10 is a member the one surface of which adheres to the face 240 of the casing 210, causing the opening 230 to be closed, and the other surface of which adheres to the skin of the living body when the biological sound is collected. The microphone 220 and the double-sided adhesive membrane 10 face each other with a space being formed therebetween. That is, the biological sound sensor 20 collects biological sounds produced in the living body while the double-sided adhesive membrane 10 is in a state of closing the opening 230.

Figure 3:
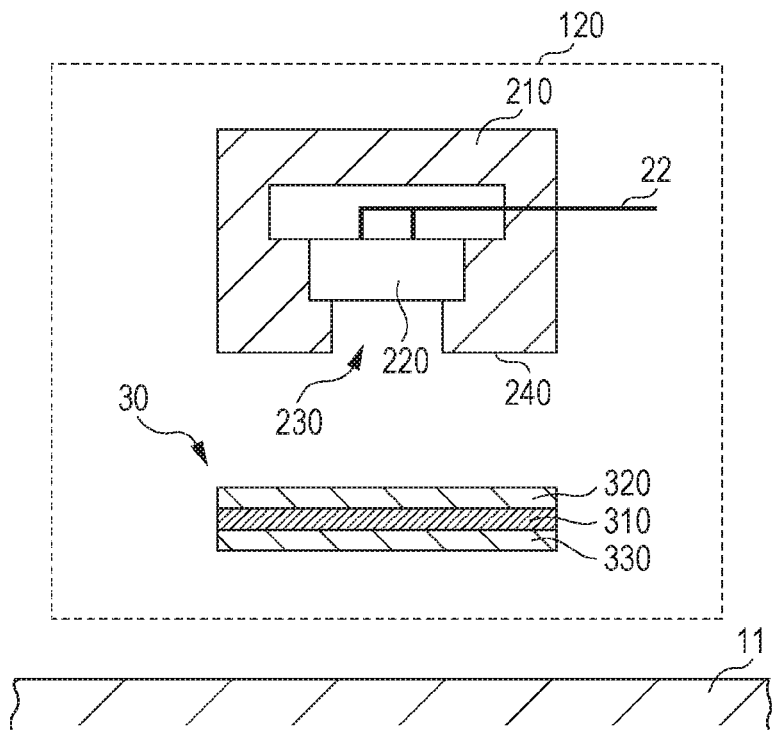
FIG. 3 is a cross-sectional view illustrating an example of a biological sound sensor and corresponding to the III-III cross section of the biological sound sensor illustrated in FIG. 2.
Figure 4:
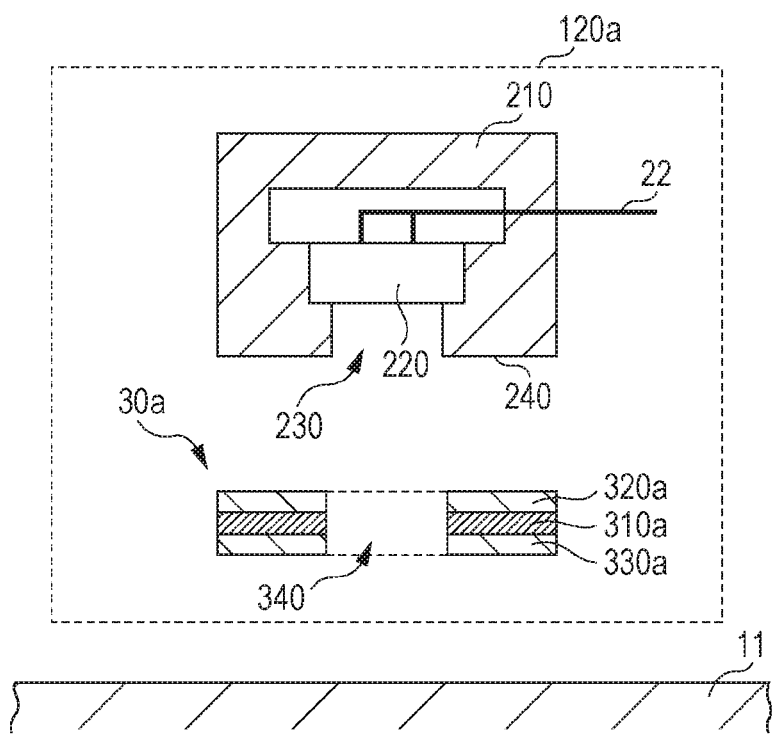
FIG. 4 is a cross-sectional view illustrating another example of a biological sound sensor and corresponding to the IV-IV cross section of the biological sound sensor illustrated in FIG. 2.

The inventor, by using biological sound sensors illustrated in FIGS. 3 and 4, measured the frequency response of an ambient noise measured by the sensors. FIG. 3 is a cross-sectional view illustrating an example of the biological sound sensor and corresponding to the III-III cross section of the biological sound sensor illustrated in FIG. 2. FIG. 4 is a cross-sectional view illustrating another example of the biological sound sensor and corresponding to the IV-IV cross section of the biological sound sensor illustrated in FIG. 2. The III-III cross section and the IV-IV cross section are cross sections when the biological sound sensor is sectioned in the direction intersecting a skin surface of the living body (the direction substantially perpendicular to the skin surface).

As illustrated in FIG. 3, a biological sound sensor 120, which is an example of the biological sound sensor 20, includes a casing 210, a microphone 220, and a double-sided adhesive membrane 30. That is, the biological sound sensor 120 uses the double-sided adhesive membrane 30 as a double-sided adhesive membrane 10 of the biological sound sensor 20. The double-sided adhesive membrane 30 is composed of a base material layer 310 which supports adhesive layers 320 and 330, both made from an adhesive material having adhesion, on both surfaces thereof.

As illustrated in FIG. 4, a biological sound sensor 120a, which is another example of the biological sound sensor 20, is a sensor which uses a double-sided adhesive membrane 30a, which is a double-sided adhesive membrane 30 of the biological sound sensor 120 in FIG. 3 to which a hole 340 is formed. The double-sided adhesive membrane 30a is composed of a base material layer 310a which supports adhesive layers 320a and 330a, both made from an adhesive material having adhesion, on both surfaces thereof, and has the hole 340 formed at the position corresponding to the opening 230 of the casing 210. In other words, the biological sound sensor 120*a* has the same structure as the biological sound sensor 120 in FIG. 3 except that the hole 340 is formed in the double-sided adhesive membrane 30*a*.

Figure 5:
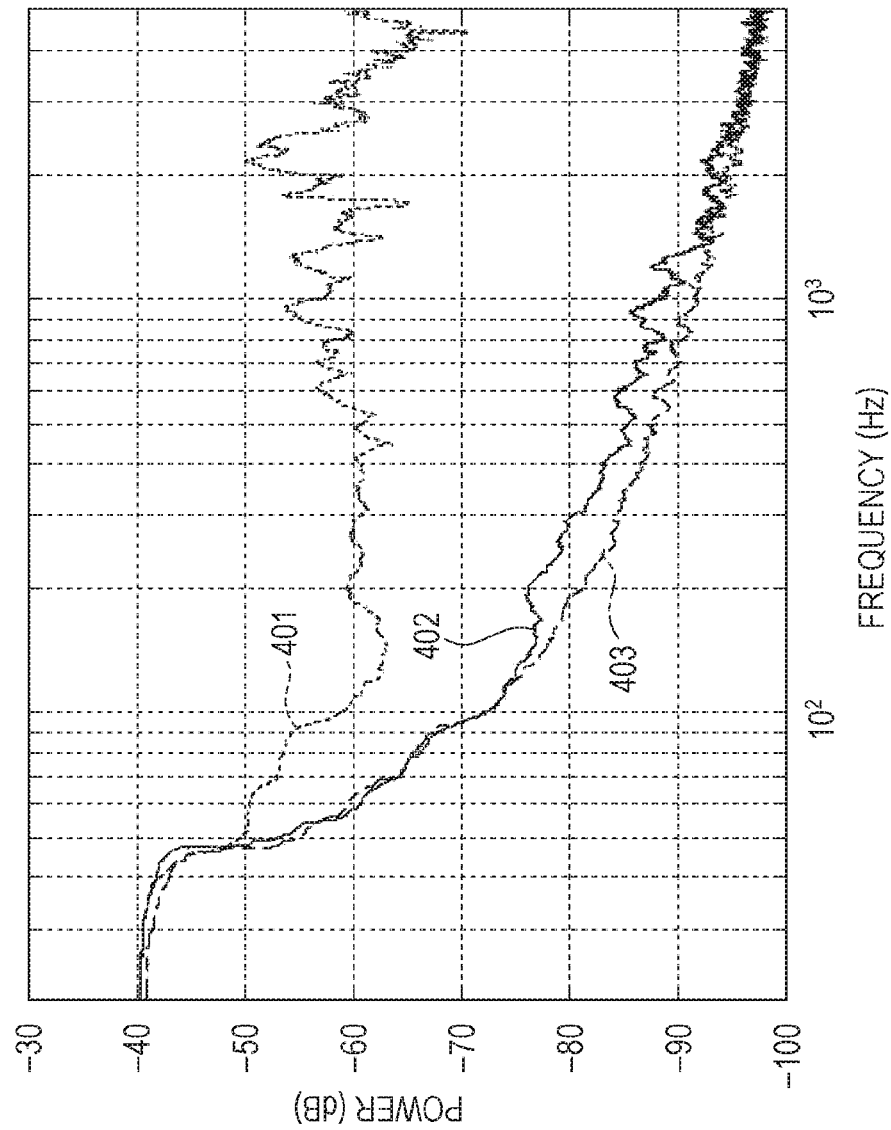
FIG. 5 is a graph illustrating a frequency response of a white noise (ambient noise) measured by the biological sound sensors in FIGS. 3 and 4.

FIG. 5 is a graph illustrating a frequency response of a white noise (ambient noise) measured by the biological sound sensor in FIG. 2 and the biological sound sensor in FIG. 3. Specifically, FIG. 5 is a graph illustrating the frequency response of the white noise (ambient noise) measured by attaching the biological sound sensor 120 in FIG. 3 and the biological sound sensor 120*a* in FIG. 4 individually to a human phantom. The white noise is an ambient noise output from an external speaker. A graph 403 in FIG. 5 shows a frequency response (frequency response of the noise level) measured by the biological sound sensors 120 and 120*a* in a silent state, that is, when no ambient noise is output. That is, because the graph 403 showing the frequency response of the noise level indicates the silent state, a sound measured with a higher level than the graph 403 indicates that an ambient noise is measured as a noise.

A graph 401, for a case in which the biological sound sensor 120*a* (FIG. 4), for which the double-sided adhesive membrane 30*a* having the hole 340 is employed, is used, indicates that an ambient noise is measured as a noise particularly for a signal with a frequency of 50 Hz or higher with respect to the graph 403 showing the frequency response of the noise level. On the other hand, a graph 402, for a case in which the biological sound sensor 120 (FIG. 3), for which the double-sided adhesive membrane 30 having no hole is employed, is used, indicates that the ambient noise is significantly reduced as compared with the graph 401 to as low as a level where a slight noise is measured for a range with a frequency of 100 Hz or higher with respect to the graph 403 showing the frequency response of the noise level.

From the results above, it is shown that resistance to ambient noise is improved significantly by closing the opening 230 of the casing 210 with the double-sided adhesive membrane 30 having no hole.

A conventional double-sided adhesive membrane is made such that a thin membrane (base material) made from resin supports an adhesive in order to maintain strength and for easier handling. However, there is a concern that, when a sound signal passes through a double-sided adhesive membrane with such a structure, reflection and absorption of the sound occur at a boundary between the adhesive and the base material, and signal strength is thus attenuated. Therefore, the inventor has studied the following measures.

A biological sound sensor according to an aspect of the present disclosure is a biological sound sensor to be used in contact with a skin of a living body, and includes a casing that has an opening in a face on the side facing the skin of the living body, a double-sided adhesive membrane both surfaces of which have adhesion, one surface of which closes the opening by adhering to the face of the casing, and the other surface of which adheres to the skin when collecting a biological sound produced in the living body, and a microphone that is arranged in the casing and picks up the biological sound. The double-sided adhesive membrane has a one-material portion that is made from a single type of material across the entire width in the thickness direction and is made from an adhesive material.

According to this configuration, a double-sided adhesive membrane is mounted on a face of the casing of the biological sound sensor on the side contacting the skin of the living body. The double-sided adhesive membrane has a one-material portion that is made from a single type of material across the entire width in the thickness direction. As described above, because the double-sided adhesive membrane is configured to be mounted on the face on the side, contacting the skin of the living body, of the casing, the casing is caused to adhere to the skin by the double-sided adhesive membrane. With this configuration, because the double-sided adhesive membrane closely adheres to the skin even when the surface of the skin is deformed, it is possible to prevent the casing from separating from the skin surface.

Because the double-sided adhesive membrane is configured to be attached by adhering to only a face of the casing, the double-sided adhesive membrane is easily removed from the casing. That is, it is possible to replace the double-sided adhesive membrane easily.

Because the double-sided adhesive membrane includes a one-material portion that is made from a single type of material across the entire width in the thickness direction, and does not have a hole, it is possible to collect a biological sound sensitively without being significantly influenced by an ambient noise. In consequence, by using a biological sound sensor for which such a double-sided adhesive membrane is employed, it is possible to measure a biological sound with a high SN ratio.

For example, the double-sided adhesive membrane may be made from only the adhesive material.

Therefore, it is possible to form a double-sided adhesive membrane having a one-material portion easily.

For example, the double-sided adhesive membrane may further include a base material layer which contains a meshed sheet and, at least on the side of the base material layer contacting the skin, an adhesive layer made from the adhesive material is formed.

With this configuration, because the double-sided adhesive membrane includes a base material layer containing a meshed sheet, it is possible to make the double-sided adhesive membrane have a structure that is resistant to damage. In addition, because the double-sided adhesive membrane includes a one-material portion, it is possible to prevent a reduction in the sensitivity for biological sound.

For example, the double-sided adhesive membrane may further include a base material layer that contains a sheet in which a hole is formed and, at least on the side of the base material layer contacting the skin, an adhesive layer made from the adhesive material is formed.

With this configuration, because the double-sided adhesive membrane includes a base material layer containing a sheet in which a hole is formed, it is possible to make the double-sided adhesive membrane have a structure that is resistant to damage. In addition, because the double-sided adhesive membrane includes a one-material portion, it is possible to prevent a reduction in the sensitivity for biological sound.

For example, on the surface of the double-sided adhesive membrane contacting the skin, a lattice-shaped pattern or a plurality of dot patterns may be printed.

In consequence, a user is able to judge whether or not the double-sided adhesive membrane is broken or deformed by visually checking the shape of the lattice-shaped pattern or the plurality of dot patterns. With this configuration, because the double-sided adhesive membrane may be replaced with a new double-sided adhesive membrane when the double-sided adhesive membrane is broken or deformed, it is possible to measure a biological sound with good precision.

For example, the microphone and the double-sided adhesive membrane may face each other.

For example, the casing may be made of a first casing and a second casing, the second casing may include the opening, and the second casing may be detachable from the first casing.

In consequence, it is further possible to use the second casing as a disposable component and it is thus possible, for example, to replace the second casing, which is positioned on the side contacting the skin, at every measurement. Because this configuration makes it possible to keep the second casing on the side contacting the skin to be a new casing at all times, it is sanitary.

For example, the microphone may be arranged in the second casing.

In consequence, it is possible, for example, to use a new microphone at every measurement by replacing the second casing, making it possible to avoid a measurement error, caused by a variation in a sensitivity characteristic due to aging degradation of a microphone.

For example, the microphone may be arranged in the first casing.

For example, the double-sided adhesive membrane may be mounted on the second casing in advance.

In consequence, it is possible to save the efforts of a user correctly attaching the double-sided adhesive membrane, which is difficult to handle. Therefore, it is possible to use a correctly attached second casing at all times, making it possible to measure a biological sound with good precision.

The present disclosure may be embodied as a biological sound diagnostic device that includes the above-described biological sound sensor and a main body that analyzes a sound collected by the biological sound sensor and outputs an analyzed result.

First Embodiment

A biological sound sensor 20a of a first embodiment will be described. The biological sound sensor 20a is an example of the biological sound sensor 20, which is a component of the biological sound diagnostic device 2 described above. That is, the biological sound diagnostic device 2 including a biological sound sensor will also be used in the first embodiment as with the above description.

Figure 6:
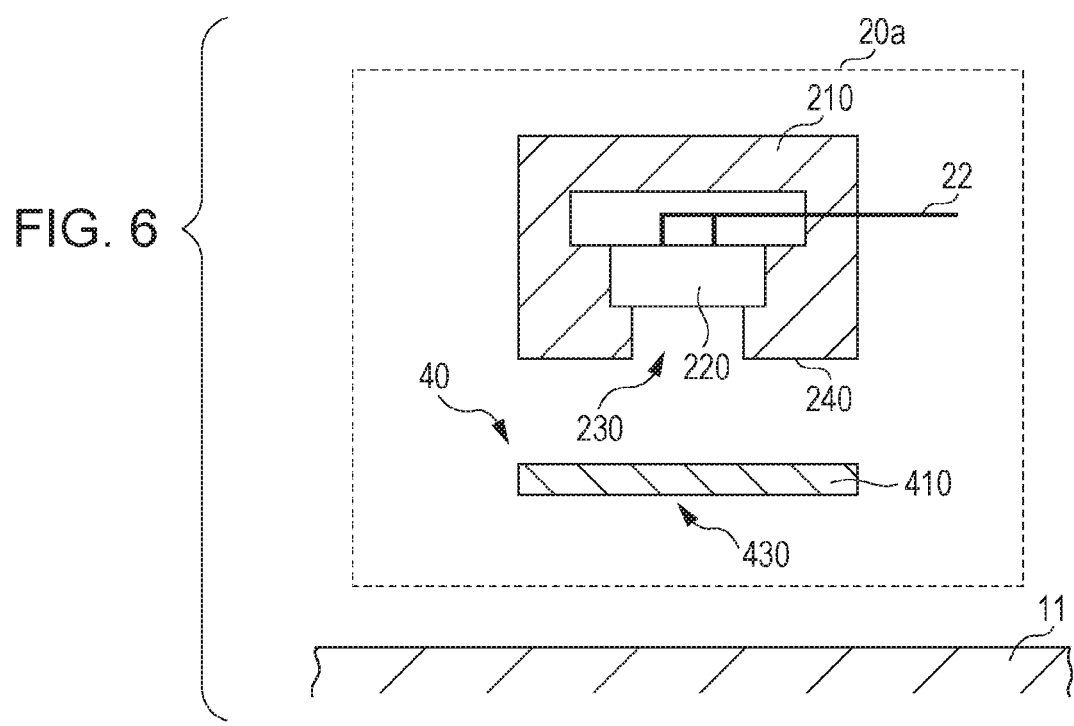
FIG. 6 is a cross-sectional view illustrating a biological sound sensor of a first embodiment and corresponding to the VI-VI cross section of the biological sound sensor illustrated in FIG. 2.

FIG. 6 is a cross-sectional view illustrating a biological sound sensor of the first embodiment and corresponding to the VI-VI cross section of the biological sound sensor illustrated in FIG. 2. For the biological sound sensor 20a, a double-sided adhesive membrane 40, which is made of only an adhesive layer 410 made from an adhesive material having adhesion, is employed as a double-sided adhesive membrane 10. The biological sound sensor 20a has the same configuration as the biological sound sensor 20 except the double-sided adhesive membrane 40. The double-sided adhesive membrane 40 includes a one-material portion 430 that is made from a single type of adhesive material across the entire width in the thickness direction. The adhesive material that forms the double-sided adhesive membrane 40, that is, the adhesive layer 410 is an adhesive hydrocolloid material, an adhesive hydrogel material, synthetic rubber, or the like. That is, the double-sided adhesive membrane 40 is made from a material (i) that is able to maintain a shape by itself or restore a shape even if a certain force is applied and (ii) the surface of which has a stickiness or an adhesiveness.

Figure 7:
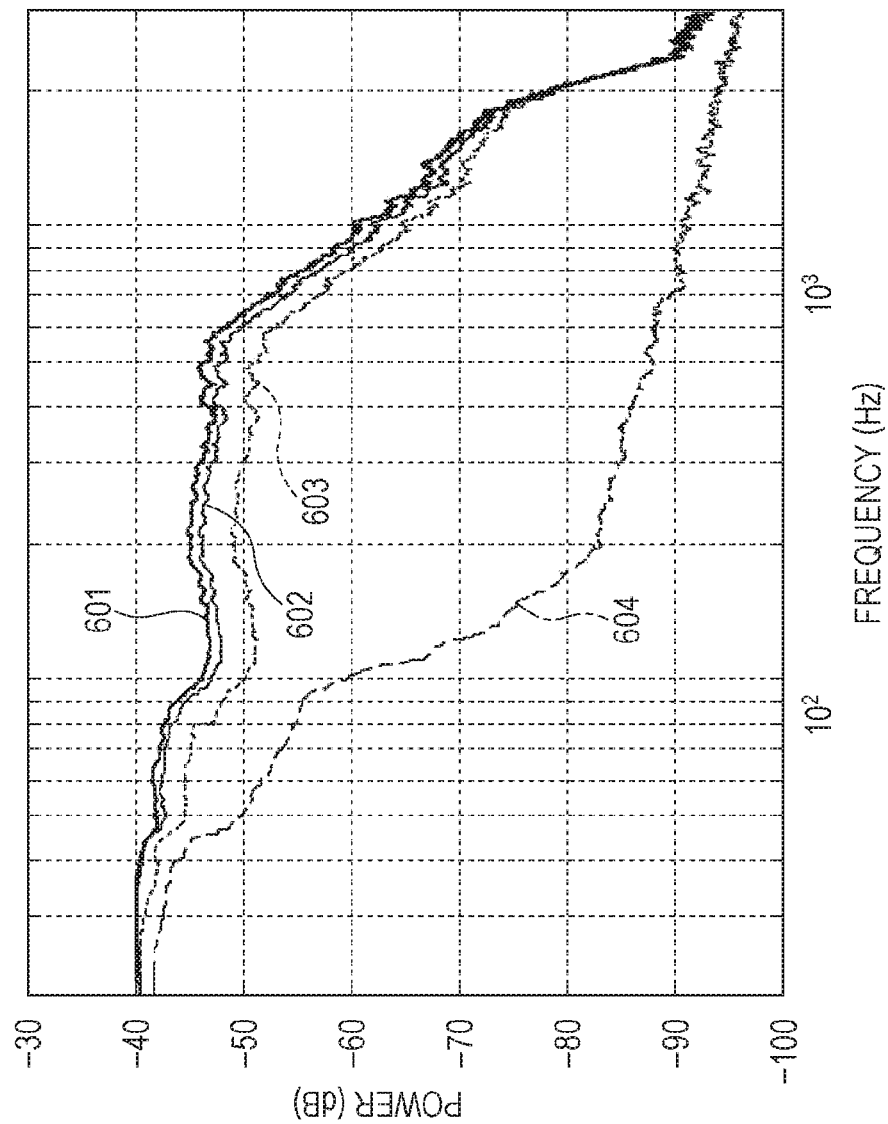
FIG. 7 is a graph illustrating frequency responses of sensitivities for biological sounds which are individually measured by the biological sound sensors illustrated in FIGS. 3, 4, and 6.

FIG. 7 is a graph illustrating frequency responses of sensitivities for biological sounds which are individually measured by the biological sound sensors illustrated in FIGS. 3, 4, and 6. That is, FIG. 7 is a graph illustrating a frequency response of a sensitivity for a biological sound measured by using the biological sound sensor 120a for which the double-sided adhesive membrane 30a having the hole 340 is employed, a frequency response of a sensitivity for the biological sound measured by using the biological sound sensor 120 for which the double-sided adhesive membrane 30 including the base material layer 310 and having no hole is employed, and a frequency response of a sensitivity for the biological sound measured by using the biological sound sensor 20a for which the double-sided adhesive membrane 40 made of only the adhesive layer 410 and having no hole is employed. Specifically, the frequency response of the sensitivity for the biological sound when the biological sound is measured by using the biological sound sensor 120a is illustrated by a graph 601. The frequency response of the sensitivity for the biological sound when the biological sound is measured by using the biological sound sensor 120 is illustrated by a graph 603. The frequency response of the sensitivity for the biological sound when the biological sound is measured by using the biological sound sensor 20a is illustrated by a graph 602. A graph 604 illustrates a frequency response (frequency response of the noise level) measured by the microphones 220 of the biological sound sensors 20a, 120, and 120a in a silent state.

As illustrated in FIG. 7, it is understood that, among three types of biological sound sensors 20a, 120, and 120a, when the biological sound sensor 120a, for which the double-sided adhesive membrane 30a having the hole 340 is employed, is used, the sensitivity takes the highest value, and, when biological sound sensor 120, for which the double-sided adhesive membrane 30 including the base material layer 310 and having no hole is employed, is used, the sensitivity is reduced significantly. On the other hand, when the biological sound sensor 20a, for which the double-sided adhesive membrane 40 made of only the adhesive layer 410 and having no hole is employed, is used, the sensitivity reduction is comparatively smaller than a case in which the biological sound sensor 120 is used. As examined in FIG. 5, considering that the biological sound sensor 120a, for which the double-sided adhesive membrane 30a having the hole 340 is employed, is significantly influenced by an ambient noise, it is preferable to use, in a general noise environment, a biological sound sensor for which a double-sided adhesive membrane that has no hole is employed. In other words, when the biological sound sensor 20a, for which the double-sided adhesive membrane 40 made of only the adhesive layer 410 and having no hole is employed, is used, it is possible to collect a biological sound sensitively without being influenced by an ambient noise significantly. In consequence, it is possible to measure a biological sound with a high SN ratio.

As described above, when the biological sound sensor 20a, for which the double-sided adhesive membrane 40 made of only the adhesive layer 410 and having no hole is employed, is used, it becomes possible to examine a biological sound with a comparatively low signal level, such as a small respiratory sound, a respiratory sound in the lung base, and a blood flow sound, even in a noise environment.

According to the biological sound sensor 20a of the first embodiment, the double-sided adhesive membrane 40 is mounted to the casing 210 of the biological sound sensor 20a on the face 240 that is the side contacting the skin 11 of the living body. The double-sided adhesive membrane 40 is made of only the adhesive layer 410, which is an adhesive material. As described above, because the double-sided adhesive membrane 40 is configured to be mounted on the face 240 of the casing 210 on the side adhering to the skin 11 by the double-sided adhesive membrane 40, the casing 210 is caused to adhere to the skin 11 by the double-sided adhesive membrane 40. With this configuration, because, even if the surface of the skin 11 is deformed, the double-sided adhesive membrane 40 keeps fluidity or elasticity and the surface thereof adheres tightly to the skin 11, it is possible to prevent the casing 210 from separating from the skin.

According to the biological sound sensor 20a of the first embodiment, because the double-sided adhesive membrane 40 is configured to be mounted by adhering to only the face 240 of the casing 210, the double-sided adhesive membrane 40 may be removed from the casing 210 easily. In other words, it is possible to replace the double-sided adhesive membrane 40 easily.

Second Embodiment

A biological sound sensor 20b of a second embodiment will be described. The biological sound sensor 20b is an example of the biological sound sensor 20, which is a component of the biological sound diagnostic device 2 described above. That is, the biological sound diagnostic device 2 including a biological sound sensor is also used in the second embodiment as with the above description.

Figure 8A:
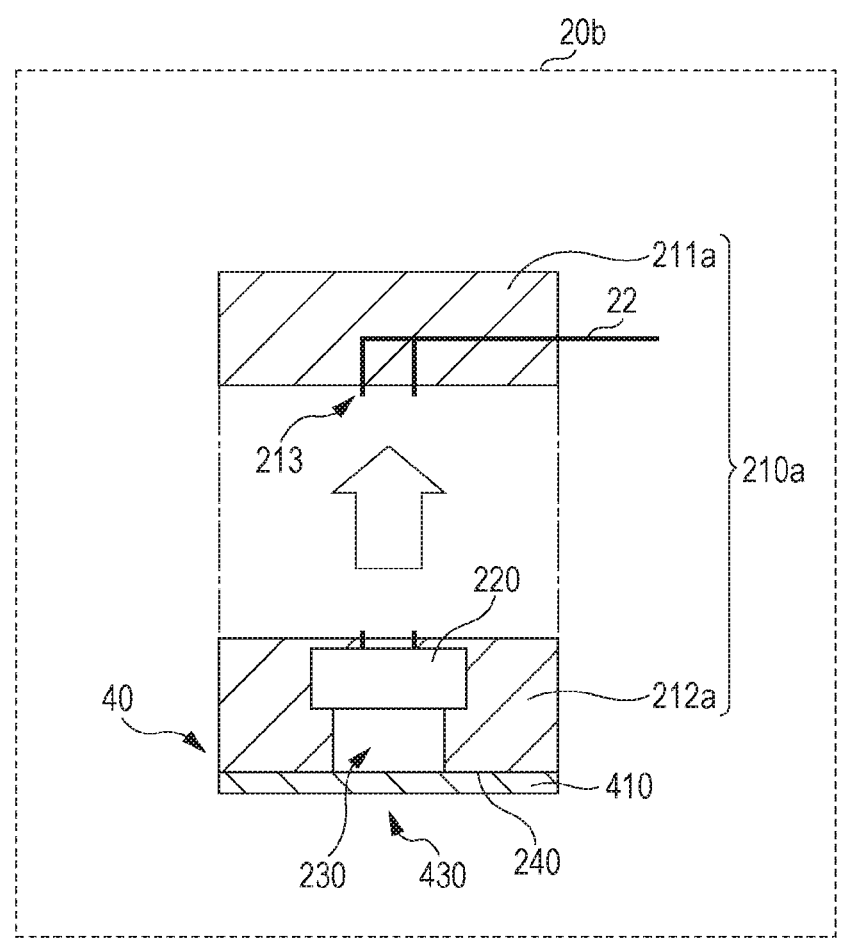
FIG. 8A is a cross-sectional view illustrating a biological sound sensor of a second embodiment and corresponding to the VIIIA-VIIIA cross section of the biological sound sensor illustrated in FIG. 2.

FIG. 8A is a cross-sectional view illustrating the biological sound sensor of the second embodiment and corresponding to the VIIIA-VIIIA cross section of the biological sound sensor illustrated in FIG. 2. The biological sound sensor 20b differs from the biological sound sensor 20a of the first embodiment in that a casing 210a that is separable into a first casing 211a on the main body side and a second casing 212a on the skin side is employed. The second casing 212a has an opening 230. A microphone 220 is mounted to the second casing 212a. A signal cable 22 in the first casing 211a and the microphone 220 in the second casing 212a are electrically detachable from each other by a connector 213. Because the configuration of other portions is the same as the configuration of the biological sound sensor 20a of the first embodiment, the same component will be denoted by the same reference character and description thereof will be omitted.

A main body side portion of the biological sound sensor 20b includes the first casing 211a and the signal cable 22 through which a sound signal (analog signal) is transmitted to a main body 21. On the other hand, a skin side portion of the biological sound sensor 20b includes the second casing 212a that has the opening 230, the microphone 220 that picks up a biological sound, and a double-sided adhesive membrane 40. The casing 210a of the biological sound sensor 20b is separable into the first casing 211a and the second casing 212a, which makes it possible to provide the second casing 212a as a replaceable and disposable sensor for every measurement of a biological sound. That is, the second casing 212a is detachable from the first casing 211a.

In this case, the double-sided adhesive membrane 40 may be provided to a user while being attached in advance with proper adhesion pressure at a proper position on a face 240 so as to close the opening 230 of the second casing 212a.

According to the biological sound sensor 20b of the second embodiment, it is possible to use a second casing as a disposable component and, for example, replace a second casing, which is located on the side contacting a skin, for every measurement. Because this configuration makes it possible to keep the second casing on the side contacting the skin to be a new casing at all times, it is sanitary.

According to the biological sound sensor 20b of the second embodiment, it is possible to replace a whole of the second casing 212a including the microphone 220 for every measurement, making it possible to use a new microphone and prevent a measurement error caused by a variation in a sensitivity characteristic due to aging degradation of a microphone.

The double-sided adhesive membrane 40 may be mounted on the second casing 212a in advance. The double-sided adhesive membrane 40 is soft and breakable and thus difficult to handle. Therefore, mounting a double-sided adhesive membrane to a casing in advance and providing the mounted double-sided adhesive membrane makes it possible to prevent an unintended tear and split, which may occur when a double-sided adhesive membrane is attached to a sensor, and thus prevent an ambient noise from being mixed in.

Variation of Second Embodiment

A biological sound sensor 20c according to a variation of the second embodiment will be described. The biological sound sensor 20c is an example of the biological sound sensor 20, which is a component of the biological sound diagnostic device 2 described above.

Figure 8B:
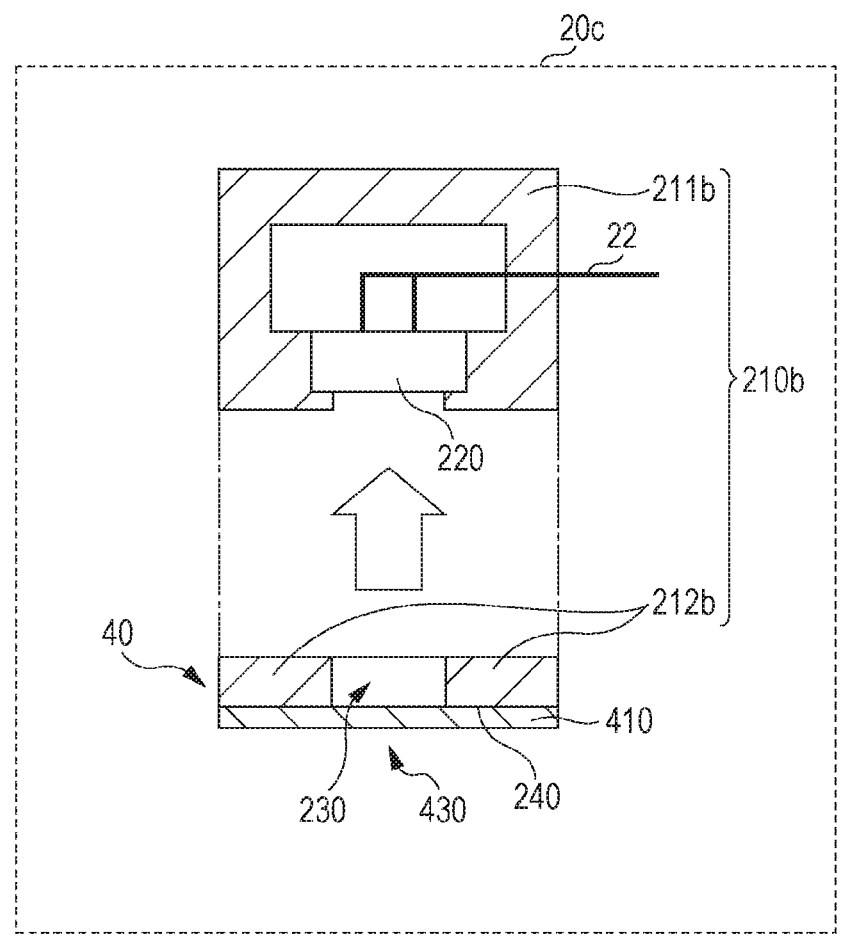
FIG. 8B is a cross-sectional view illustrating a biological sound sensor of a variation of the second embodiment and corresponding to the VIIIB-VIIIB cross section of the biological sound sensor illustrated in FIG. 2.

FIG. 8B is a cross-sectional view illustrating a biological sound sensor of the variation of the second embodiment and corresponding to the VIIIB-VIIIB cross section of the biological sound sensor illustrated in FIG. 2. The biological sound sensor 20c is the same as the biological sound sensor 20b of the second embodiment in that a casing 210b of the biological sound sensor 20c is separable into a first casing 211b on the main body side and a second casing 212b on the skin side. However, the biological sound sensor 20c differs from the biological sound sensor 20b of the second embodiment in that a microphone 220 is mounted on the first casing 211b, not the second casing 212b. Because the configuration of other portions is the same as the configuration of the biological sound sensor 20b of the second embodiment, the same component will be denoted by the same reference character and description thereof will be omitted.

For a biological sound sensor 20c according to the variation of the second embodiment, it is possible to provide a ring-shaped second casing 212b, to which the double-sided adhesive membrane 40 is attached in advance, as a disposable attaching unit, making it possible to replace the second casing 212b for every measurement. In this case, because the microphone 220 is not included in the second casing 212b, which is used as a disposable component, it is possible to measure a biological sound at low cost, with ease, and with a high SN ratio.

The double-sided adhesive membrane 40 may be mounted on the second casing in advance even for the biological sound sensor 20c described above. In this case, it is possible to save the effort of a user attaching the double-sided adhesive membrane 40, which is difficult to handle, to a face 240 of the second casing 212b accurately. Therefore, it is possible to use the accurately attached second casing 212b at all times, making it possible to measure a biological sound with good precision.

In the second embodiment and variation thereof, the first casings 211a and 211b and the second casings 212a and 212b may be connected, for example, by screwing, by press-fit, or by snap-fit. That is, it is sufficient for the first casings 211a and 211b and the second casings 212a and 212b to be connected in a manner of being repeatedly detachable, and employing a specific connection configuration is not required. Because the first casings 211a and 211b are connected to a plurality of second casings 212a and 212b, it is preferable that the first casings 211a and 211b are made from a material with a higher hardness than the second casings 212a and 212b.

Other Embodiments

Although, in the above-described embodiments and variation thereof, the double-sided adhesive membrane 40, which is made of only an adhesive layer 410, is employed as a double-sided adhesive membrane 10 used in the biological sound sensor 20, the configuration is not limited to this configuration.

Other Embodiment 1

Figure 9A:
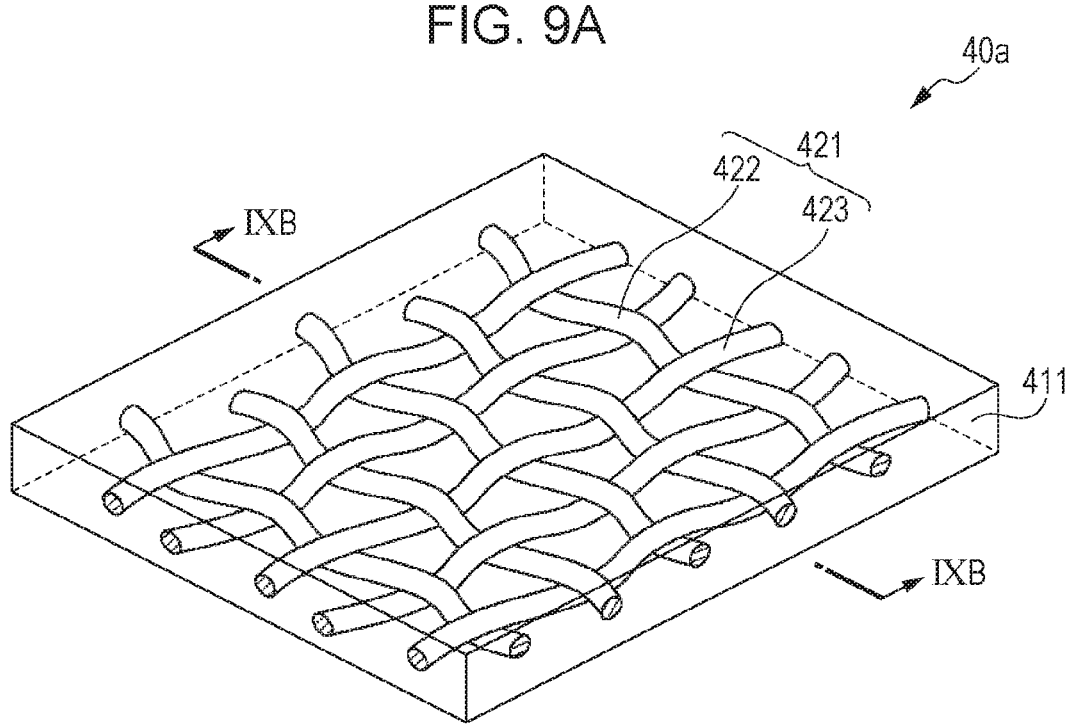
FIG. 9A is an enlarged partly cutaway perspective view illustrating a portion of a double-sided adhesive membrane according to other embodiment 1.
Figure 9B:
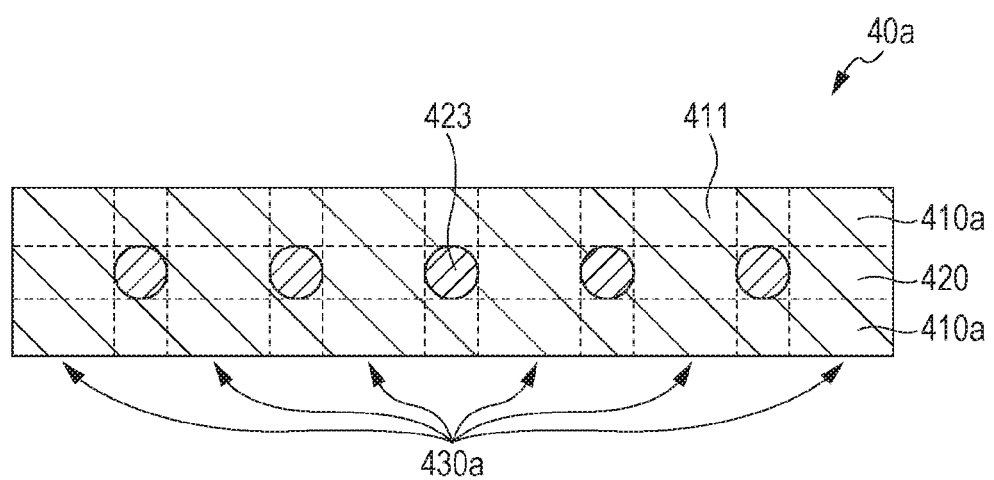
FIG. 9B is a cross-sectional view illustrating a cross section taken along the line IXB-IXB in FIG. 9A.

FIG. 9A is an enlarged partly cutaway perspective view illustrating a portion of a double-sided adhesive membrane according to other embodiment 1. FIG. 9B is a cross-sectional view illustrating a cross section taken along the line IXB-IXB in FIG. 9A.

As illustrated in FIGS. 9A and 9B, a double-sided adhesive membrane 40a, which has a base material layer 420 including a meshed sheet 421 and an adhesive layer 410a made from an adhesive material 411 formed at least on the side of the base material layer 420 contacting a skin, may also be employed as a double-sided adhesive membrane 10. Specifically, the double-sided adhesive membrane 40a has the adhesive layers 410a formed on both sides of the meshed sheet 421 and the interspace of the mesh is filled with the adhesive material 411. In other words, as illustrated in FIG. 9B, the double-sided adhesive membrane 40a includes a one-material portion 430a that is made from a single type of material across the entire width in the thickness direction.

The meshed sheet 421 illustrated in FIG. 9A is a sheet woven with a plurality of warp fibers 422 and a plurality of weft fibers 423. The meshed sheet does not have to be a sheet woven with a plurality of warp fibers 422 and a plurality of weft fibers 423, and may be a sheet woven with a warp fiber and a weft fiber or a meshed sheet that has other types of fabric structures.

As described above, because the double-sided adhesive membrane 40a has the base material layer 420 including the meshed sheet 421, it is possible to make the double-sided adhesive membrane 40a to be a structure that is hard to break. Because the double-sided adhesive membrane 40a has the one-material portion 430a, it is possible to prevent a reduction in the sensitivity for biological sounds.

Other Embodiment 2

Figure 10A:
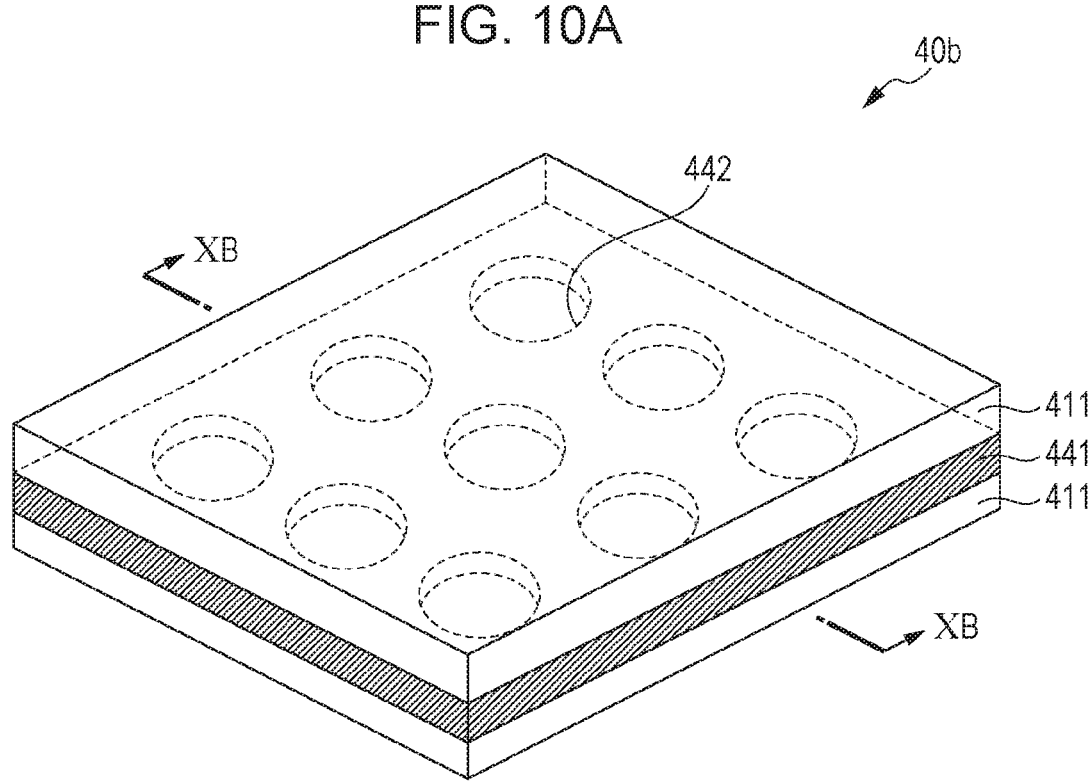
FIG. 10A is an enlarged partly cutaway perspective view illustrating a portion of a double-sided adhesive membrane according to other embodiment 2.
Figure 10B:
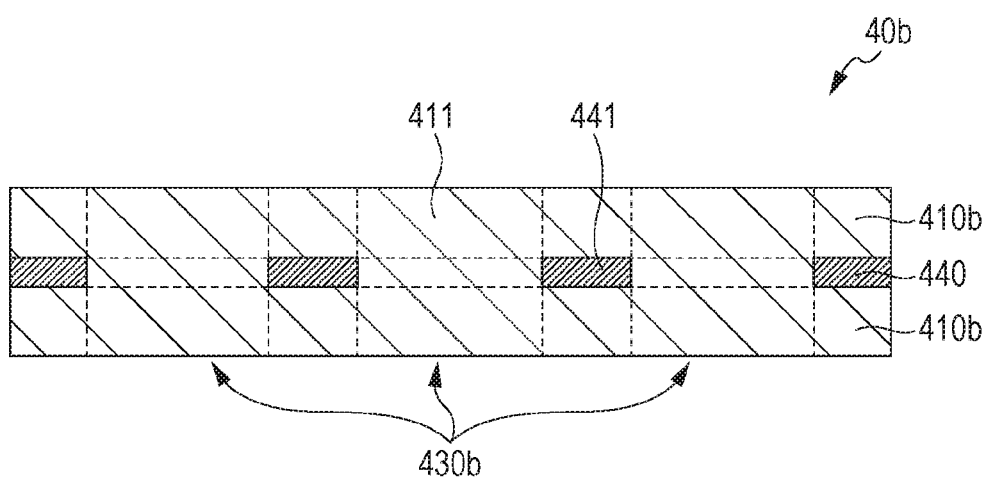
FIG. 10B is a cross-sectional view illustrating a cross section taken along the line XB-XB in FIG. 10A.

FIG. 10A is an enlarged partly cutaway perspective view illustrating a portion of a double-sided adhesive membrane according to other embodiment 2. FIG. 10B is a cross-sectional view of a cross section taken along the line XB-XB in FIG. 10A.

As illustrated in FIGS. 10A and 10B, a double-sided adhesive membrane 40b, which has a base material layer 440 including a sheet 441 in which a plurality of holes 442 are formed and an adhesive layer 410b made from an adhesive material 411 formed at least on the side of the base material layer 440 contacting a skin, may also be employed as a double-sided adhesive membrane 10. Specifically, the double-sided adhesive membrane 40b has the adhesive layers 410b formed on both sides of the sheet 441 and spaces created by the plurality of holes 442 are filled with the adhesive material 411. That is, as illustrated in FIG. 10B, the double-sided adhesive membrane 40b has a one-material portion 430b that is made from a single type of material across the entire width in the thickness direction. Although the shapes of the plurality of holes 442 formed in the sheet 441 illustrated in FIG. 10A are round, the shapes may be elliptical or polygonal, that is, having a specific shape is not required.

As described above, because the double-sided adhesive membrane 40b has the base material layer 440 including the sheet 441 in which the plurality of holes 442 are formed, it is possible to make the double-sided adhesive membrane 40b to be a structure that is hard to break. Because the double-sided adhesive membrane 40b also has the one-material portion 430b, it is possible to prevent a reduction in the sensitivity for biological sounds.

Other Embodiment 3

Figure 11:
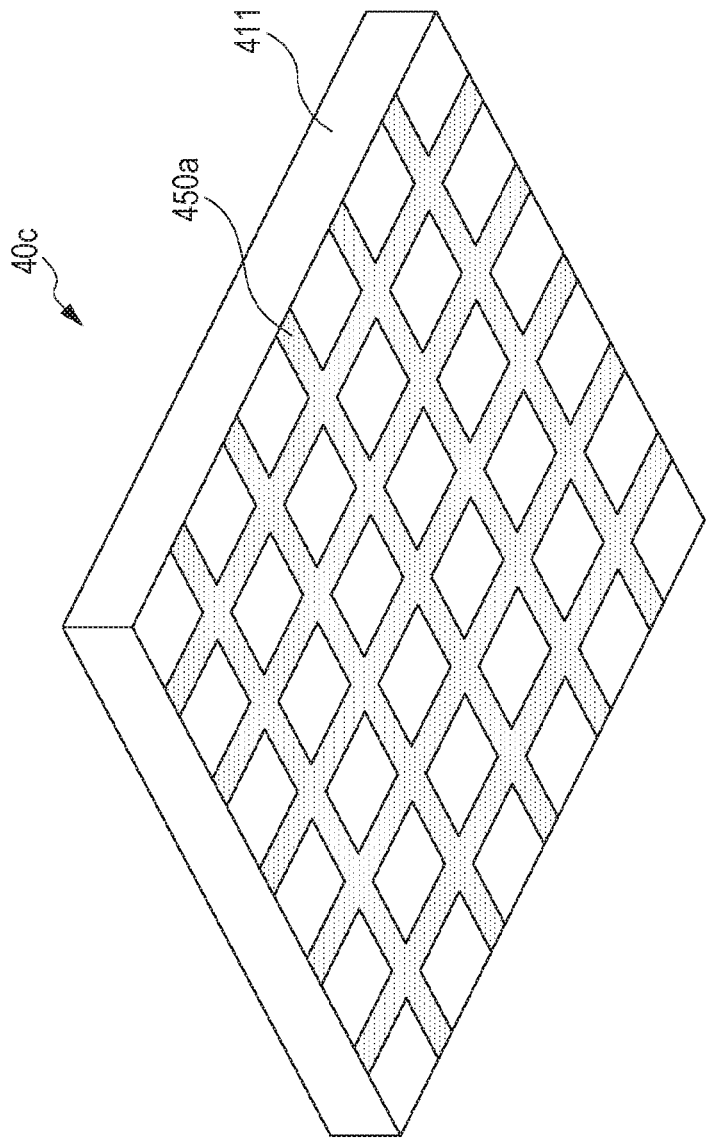
FIG. 11 is an enlarged partly cutaway perspective view illustrating a portion of a double-sided adhesive membrane according to other embodiment 3.

FIG. 11 is an enlarged partly cutaway perspective view illustrating a portion of a double-sided adhesive membrane according to other embodiment 3. FIG. 12 is an enlarged partly cutaway perspective view illustrating a portion of another double-sided adhesive membrane according to other embodiment 3.

As illustrated in FIG. 11, a double-sided adhesive membrane 40c, which has a lattice-shaped pattern 450a printed on a surface contacting a skin, may be employed as a double-sided adhesive membrane 10. As illustrated in FIG. 12, a double-sided adhesive membrane 40d, which has a plurality of dot patterns 450b printed on a surface contacting a skin, may also be employed as a double-sided adhesive membrane 10. Both the double-sided adhesive membranes 40c and 40d are made of only an adhesive layer made from an adhesive material 411. The portion on which the patterns are printed may have a configuration in which a printed layer is formed on a surface of the adhesive layer or a configuration in which the patterns are printed with a material identical to the material of the adhesive layer.

In consequence, a user is able to judge whether or not the double-sided adhesive membranes 40c and 40d are broken or deformed by visually checking the printing of the lattice-shaped pattern 450a or the plurality of dot patterns 450b. With this configuration, because when the double-sided adhesive membranes 40c and 40d are broken or deformed, the double-sided adhesive membranes 40c and 40d can be replaced with new double-sided adhesive membranes 40c and 40d, it is possible to measure a biological sound with good precision.

The present disclosure is useful as a biological sound sensor, a biological sound diagnostic device including the biological sound sensor, and the like that make it easy to replace an adhesive member and cause a casing to be hard to separate from a skin surface of a living body.

What is claimed is:

1. A biological sound sensor to be used in contact with a skin of a living body comprising:
   a casing that has an opening in a face on a side facing the skin of the living body;
   a microphone that is arranged in the casing and picks up a biological sound; and
   a double-sided adhesive membrane having (i) a first surface configured to adhere to the skin in a state of collecting the biological sound produced in the living body and (ii) a second surface which closes the opening by adhering to the face of the casing, the double-sided adhesive membrane including:
a first adhesive layer on the first surface, the first adhesive layer which is made of a first adhesive material having adhesion;
a second adhesive layer on the second surface, the second adhesive layer which is made of the first adhesive material; and
a base material layer which is sandwiched between the first adhesive layer and the second adhesive layer,
wherein the base material layer includes holes which are filled with the first adhesive material,
wherein the double-sided adhesive membrane has an one-material portion, made of the first adhesive material, through the double-sided adhesive membrane from the first surface to the second surface.

2. The biological sound sensor according to claim 1, wherein, on the first surface, a lattice-shaped pattern or a dot patterns is printed.

3. The biological sound sensor according to claim 1, wherein
the casing is made of a first casing and a second casing,
the second casing includes the opening,
the second casing is detachable from the first casing, and
the first casing includes signal cable through which a sound signal, generated at the microphone, is transmitted.

4. The biological sound sensor according to claim 1, wherein
the casing is made of a first casing and a second casing,
the second casing includes the opening,
the second casing is detachable from the first casing, and
the first casing includes the microphone.

5. The biological sound sensor according to claim 4, wherein
the second casing is a disposal attachment unit on which the double-sided adhesive membrane is attached.

6. The biological sound sensor according to claim 1, wherein
the casing is made of a first casing and a second casing,
the second casing includes the opening,
the second casing is detachable from the first casing, and
the second casing includes the microphone.

7. A biological sound sensor to be used in contact with a skin of a living body comprising:
a casing that has an opening in a face on a side facing the skin of the living body;
a microphone that is arranged in the casing and picks up a biological sound; and
a double-sided adhesive membrane having (i) a first surface configured to adhere to the skin in a state of collecting the biological sound produced in the living body and (ii) a second surface which closes the opening by adhering to the face of the casing,
the double-sided adhesive membrane including:
a first adhesive layer on the first surface, the first adhesive layer which is made of a first adhesive material having adhesion;
a second adhesive layer on the second surface, the second adhesive layer which is made of the first adhesive material; and
a base material layer which is sandwiched between the first adhesive layer and the second adhesive layer,
wherein, the base material layer includes a meshed sheet and the first adhesive material, the meshed sheet is filled with the first adhesive material, and
wherein the meshed sheet has an upper surface and a lower surface that oppose each other, and the first adhesive material that fills the meshed sheet covers both the upper surface and the lower surface of the meshed sheet.

8. The biological sound sensor according to claim 7, wherein the double-sided adhesive membrane has an one-material portion, made of the first adhesive material, through the double-sided adhesive membrane from the first surface to the second surface.

9. The biological sound sensor according to claim 7, wherein, on the first surface, a lattice-shaped pattern or a dot patterns is printed.

10. The biological sound sensor according to claim 7, wherein
the casing is made of a first casing and a second casing,
the second casing includes the opening,
the second casing is detachable from the first casing, and
the first casing includes signal cable through which a sound signal, generated at the microphone, is transmitted.

11. The biological sound sensor according to claim 7, wherein
the casing is made of a first casing and a second casing,
the second casing includes the opening,
the second casing is detachable from the first casing, and
the first casing includes the microphone.

12. The biological sound sensor according to claim 11, wherein
the second casing is a disposal attachment unit on which the double-sided adhesive membrane is attached.

13. The biological sound sensor according to claim 7, wherein
the casing is made of a first casing and a second casing,
the second casing includes the opening,
the second casing is detachable from the first casing, and
the second casing includes the microphone.

14. A biological sound diagnostic system for measuring a biological sound of a living body comprising:
a biological sound sensor including:
a casing that has an opening in a face on a side facing a skin of the living body;
a microphone that is arranged in the casing and picks up the biological sound; and
a double-sided adhesive membrane having (i) a first surface configured to adhere to the skin in a state of collecting the biological sound produced in the living body and (ii) a second surface which closes the opening by adhering to the face of the casing,
the double-sided adhesive membrane including:
a first adhesive layer on the first surface, the first adhesive layer which is made of a first adhesive material having adhesion;
a second adhesive layer on the second surface, the second adhesive layer which is made of the first adhesive material; and
a base material layer which is sandwiched between the first adhesive layer and the second adhesive layer,
a signal processor configured to analyze the biological sound picked up at the microphone,
wherein the double-sided adhesive membrane has an one-material portion, made of the first adhesive material, through the double-sided adhesive membrane from the first surface to the second surface.

15. The biological sound diagnostic system according to claim 14, wherein
the base material layer includes a sheet having holes which are filled with the first adhesive material.

16. The biological sound diagnostic system according to claim 14, wherein
the base material layer includes a meshed sheet and the first adhesive material, the meshed sheet which is filled with the first adhesive material.

17. The biological sound diagnostic system according to claim 14, wherein
the casing is made of a first casing and a second casing,
the second casing includes the opening,
the second casing is detachable from the first casing, and
the first casing includes the microphone.

18. The biological sound diagnostic system according to claim 17, wherein
the second casing is a disposal attachment unit on which the double-sided adhesive membrane is attached.

19. The biological sound diagnostic system according to claim 17, wherein
the first casing includes signal cable through which a sound signal, generated at the microphone, is transmitted to the signal processor.

* * * * *